US008017588B2

(12) United States Patent
Takayama

(10) Patent No.: US 8,017,588 B2
(45) Date of Patent: Sep. 13, 2011

(54) CLARITHROMYCIN OR SALT THEREOF FOR USE IN THE TREATMENT OR PREVENTION OF PULMONARY DISEASE INDUCED BY DESTRUCTION OF PULMONARY ALVEOLI

(75) Inventor: Kiyoshi Takayama, Tokyo (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 131 days.

(21) Appl. No.: 11/917,845

(22) PCT Filed: Jun. 21, 2006

(86) PCT No.: PCT/JP2006/312385
§ 371 (c)(1),
(2), (4) Date: Dec. 17, 2007

(87) PCT Pub. No.: WO2006/137423
PCT Pub. Date: Dec. 28, 2006

(65) Prior Publication Data
US 2009/0088395 A1    Apr. 2, 2009

Related U.S. Application Data

(63) Continuation-in-part of application No. 11/165,201, filed on Jun. 24, 2005, now abandoned.

(51) Int. Cl.
*A61K 31/70* (2006.01)
(52) U.S. Cl. ........................................ 514/29
(58) Field of Classification Search .................. None
See application file for complete search history.

(56) References Cited

U.S. PATENT DOCUMENTS

| | | | |
|---|---|---|---|
| 4,331,803 | A | 5/1982 | Watanabe et al. |
| 5,760,010 | A | 6/1998 | Klein |
| 6,878,751 | B1 | 4/2005 | Konnelly et al. |
| 2006/0293261 | A1 | 12/2006 | Takayama |

FOREIGN PATENT DOCUMENTS

| | | |
|---|---|---|
| JP | 61-52839 | 11/1986 |
| JP | 2004-531539 | 10/2004 |
| WO | 02/087596 | 11/2002 |

OTHER PUBLICATIONS

Nakamura et al."'Effect of Levofloxacin on Theophylline Clearance During Theophylline and Clarithromycin Combination Therapy", Annals of Pharmacotherapy, 2001, vol. 35, No. 6, pp. 691-693.*
Zhong et al., "An experimental study on airway inflammation and remodeling in a rat model of chronic bronchitis and emphysema", Zhonghua Jie He He Hu Za Ahi, 2003, vol. 26, No. 12, pp. 750-755.*
Wojciechowski et al., "Pulmonary Emphysema", RT: For Decision Makers in Reseperatory Care, 2003.*
FDA product label for Biaxin® clarithromycin oral tablets, approved Oct. 12, 2000, downloaded from www.fda.gov.*
Barnes P. J. et al., "New Treatments for COPD"; Nature Reviews/Drug Discovery; vol. 1, Jun. 2002, pp. 437-446.
Barnes, P.J. et al., "Pharmacological Reviews", vol. 56, No. 4, Dec. 2004,pp. 515-548.
Banerjee, D. et al., "The Effect of Oral Clarithromycin on Bronchial Airway Inflammation in Moderate-To-Severe Stable COPD", A Randomized Controlled Trial., Treat. Respir. Med., 2004, vol. 3 No. 1, pp. 59-65.
Basyigit, I. et al., "'The Effect of Clarithromycln on Inflammatory Markers in Chronic Obstructive Pulmonary Disease: Preliminary Data", Pulmonary, The Annals of Pharmacotherapy, Sep. 2004, vol. 38, pp. 1400-1405.
Jun'ichi Kadota, "Bimansei Hansai Kikanshien (DPD) ni Taisuru Clarithromycin Choki Toyo Ryoho-Maemuki Open Shiken (4 Nenkan) ni yoru Yuyosei no Kento-", Mebio (May 10, 2005), vol. 22, No. 5, pp. 126-127.
Takashi Uehara et al., "Byotai no Mechanism Kokyuki Shikkan 4 Mansei Heisokusei Haishikkan to Bimansei Hansai Kikanshien", Medicina, 2001, vol. 38, No. 2, pp. 323-327 (Pathological Mechanisms: Respiratory Diseases), Chronic Obstructive pulmonary Disease and Diffuse Panbronchiolitis; Takashi Uehara, Kouzui Kida, Tokyo Metropolitan Geriatric Hospital, 35-2 Sakae-cho, Itabashi Ward, Tokyo 173-0015, Medician vol. 38 No. 2 Feb. 2001.
Mutsuo Yamatani, "COPD Kanja ni Taisuru Macrolide Toyo no Igi", The Journal of the Japanese Respiratory Society, 2003, vol. 41, Special Extra Issue, p. 51, "The Significance of Macrolide Administration for COPD Patients", Mutsuo Yamatani, Tohoku University Hospital School of Medicine, Dept. of Geriatric an Respiratory Medicine.
Satoru Kanno, Mansei Heisokusei Haishikkan (Mansei Kikanshien . Hai Kishu), Medicina, 1995, vol. 32, No. 12, pp. 289-293, Respiratory Diseases, Chronic Obstructive Pulmonary Disease (Chronic Bronchitis and Emphysema), Satoru Kanno, Tokyo Metropolitan Geriatric Hospital, 35-2 Sakae-cho, Itabashi Ward, Tokyo 173-0015, Medicina vol. 32, No. 12, 1995 Special Issue.
Jiro Usuki, "Shotokushu Shukushu . Byotai to Macrolide Ryoho-Mansei Kansensei Shikkan no Chiryo Senryaku Macrolide Ryoho towa", Infection and Antimicrobials (Jun. 10, 2005), vol. 8 No. 2, pp. 198-203, What is Macrolide Therapy?, Kansen to Kokinyaku, vol. 8, No. 2, 2005.

(Continued)

*Primary Examiner* — Elli Peselev
(74) *Attorney, Agent, or Firm* — Oblon, Spivak, McClelland, Maier & Neustadt, L.L.P.

(57) ABSTRACT

For the purpose of treatment and/or prevention of pulmonary disorders caused by the destruction of pulmonary alveoli resulting from smoking, air pollution, noxious gas, etc., there are provided, among others, a method of administering clarithromycin or a salt thereof to a mammal and a pharmaceutical composition comprising clarithromycin or a salt thereof.

3 Claims, 2 Drawing Sheets

OTHER PUBLICATIONS

Koichiro Nakata, "Macrolide Ryoho 20 Nen no Ayumi", The Journal of the 44th Annual Meeting of the Japanese Respiratory Society, 2004, p. 80; 20 Years of Macrolide Therapy, Koichiro Nakata, Toho University, Dept. of respiratory Medicine.

Kiyoshi Takayama, Mini-lecture, Potential treatement of non-infectious Cigarette smoke-induced emphysema (COPD) with macrolides, The Japanese Journal of Antibiotics, Macrolides, Update, Research on New Action Mechanisms of Macrolides 2005, From the archives of "The 12th Research Conference on New Action Mechanisms of Macrolides", Jul. 15-16, 2005, vol. 59, Suppl. A. (Mar. 27, 2006), Record of Oral Presentation held in "Macrolides Update" On Jul. 15, 16, in 2005.

Kiyoshi Takayama, Basic Research for Chronic Obstructive Pulmonary Disease Drug Development, Therapeutic Drug Series (2)-DOPD (1), Folia Pharmacol. Jpn. 127, 304-307 (2006), Publication.

Kiyoshi Takayama, Potential Application of Clarithromycin for Treatment of Emphysema, ES7-3, Evening Symoposium (7), Potentiality of macrolide therapy, Abstract of oral presentation made in the Academic Meeting of the Japanese Respiratory Society on Jun. 2, 2006.

Demartini, et al. "Effect of multiple doses of clarithromycin and amoxicillin on IL-6, IFN[gamma] and IL-10 plasma levels in patients with community acquired pneumonia", Journal of Chemotherapy 200402 IT, vol. 16, No. 1, Feb. 2004, pp. 82-85, XP009121874.

Banerjee, et al. "The effect of oral clarithromycin on health status and sputum bacteriology in stable COPD", Respiratory Medicine, Bailliere Tindall, London, GB, vol. 99, No. 2, Feb. 1, 2005, pp. 208-215, XP004712602.

Gotfried M. H., "Macrolides for the Treatment of Chronic Sinusitis, Asthma, and COPD", Chest 200402 US, vol. 125, No. 2 Suppl., Feb. 2004, pp. 52S-61S, XP002543120.

Database Biosis [Online] Biosciences Information Service, Philadelphia, PA, US; Dec. 2003 Zhong, et al. "An experimental study on airway inflammation and remodeling in a rat model of chronic bronchitis and emphysema." XP002543121.

Database Embase [Online] Elsevier Science Publishers, Amsterdam, NL; 2002, Keicho, et al. "Diffuse panbronchiolitis: Role of macrolides in therapy" XP002543122, Database accession No. EMB-2003346445.

* cited by examiner

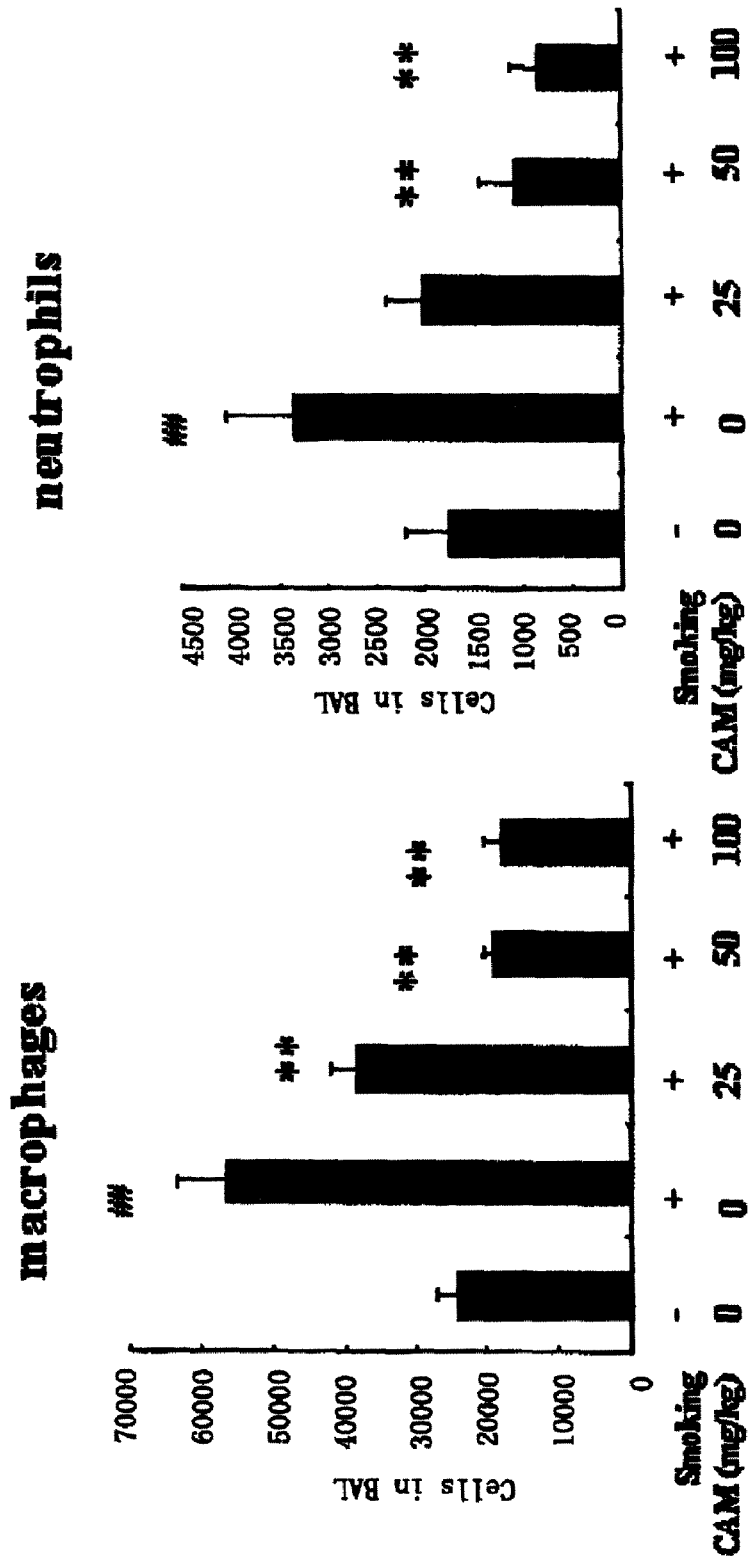

[Fig. 2]
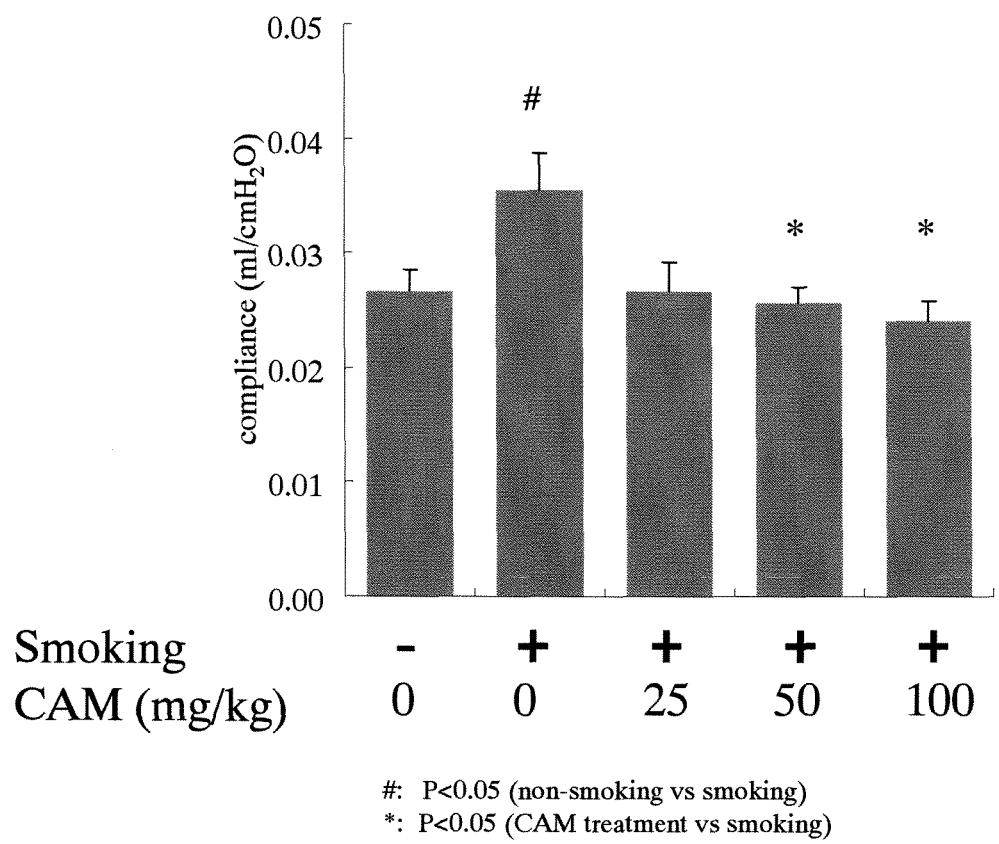
\#: P<0.05 (non-smoking vs smoking)
*: P<0.05 (CAM treatment vs smoking)

CLARITHROMYCIN OR SALT THEREOF FOR USE IN THE TREATMENT OR PREVENTION OF PULMONARY DISEASE INDUCED BY DESTRUCTION OF PULMONARY ALVEOLI

TECHNICAL FIELD

This invention relates to the use of clarithromycin or a salt thereof for the treatment or prevention of pulmonary disorders caused by the destruction of pulmonary alveoli. More particularly, it relates to a therapeutic or prophylactic agent comprising as an effective ingredient, clarithromycin or a salt thereof, a pharmaceutical composition comprising clarithromycin or a salt thereof, and a method of administering clarithromycin or a salt thereof to a mammal, for the purpose of such treatment or prevention, as well as to the use of clarithromycin or a salt thereof in the manufacture of a medicament.

BACKGROUND ART

The lung branches out from bronchi and is gradually subdivided finely to form the eventual baggy structures which are referred to as "alveoli (or alveolus)". The alveolus is composed of alveolar epithelial cells, vascular cells, and extracellular matrices (such as elastin or collagen). The alveolus is an important site where gas exchange in the body is conducted.

Pulmonary emphysema is a symptom where the alveolar walls are destroyed and the microstructures of the alveoli are hollowed out. Pulmonary emphysema reduces gas exchange efficiency and the elastic recoil of the whole lung, and it eventually lowers pulmonary functions.

It was known that inflammatory cells, such as alveolar macrophages or neutrophiles recruited into the lung, were strongly implicated in pulmonary emphysema which were activated by smoking, air pollution, noxious gas or the like (Barnes, P. J. et al., Nature Reviews/Drug Discovery, Vol. 1, 437-446 (2002)). It was reported that the macrophages and neutrophiles were activated by harmful substances in tobacco smoke or polluted air (although the detailed mechanism is unknown) and released substances (such as cytokines or proteases) capable of enhancing inflammation to take part in the destruction of the alveolar walls (Barnes, P. J. et al., Pharmacol Rev. 2004 December; 56(4):515-48).

At present, bronchodilators which improve the restriction of airflow, such as anticholinergic agents and β2 receptor stimulants, are widely used as therapeutic agents for pulmonary emphysema. However, they have not been able to alleviate the destruction of pulmonary alveoli and to retard the progression of the pulmonary emphysema itself. The use of anti-inflammatory agents represented by steroids is recommended in the acute exacerbation stage of chronic obstructive pulmonary diseases (COPD), i.e., cases involving infection and deterioration of pulmonary functions. It has, however, been reported that they are ineffective against the pulmonary emphysema itself. As pertinent art, azithromycins having a 15-membered ring were reported to display effectiveness against non-infectious inflammatory diseases (Japanese Published Application 2004-531539; JPA2004531539 or WO2002/087596). However, it was also pointed out that 14-membered macrolides differ from 15-membered macrolides with respect to pharmacological actions including anti-inflammatory action (ibid.).

DISCLOSURE OF INVENTION

Problems to be Solved

It is an object of this invention to provide a therapeutic or prophylactic agent for a pulmonary disorder caused by the destruction of pulmonary alveoli.

Means for Solving the Problems

As a result of intensive and diligent research, the present inventors have accomplished this invention upon finding that clarithromycin reduces inflammatory reaction to improve a pulmonary emphysema condition in model mice with tobacco-smoke induced pulmonary emphysema mimicking human pulmonary emphysema and that clarithromycin is useful as a therapeutic or prophylactic agent for a pulmonary disease (particularly, pulmonary emphysema).

Specifically, this invention provides a method for treating or preventing a pulmonary disorder caused by the destruction of pulmonary alveoli in a mammal (principally, in human) in need of such treatment or prevention, the method comprising administering to the mammal, an effective amount of clarithromycin or a salt thereof.

This invention also provides a pharmaceutical composition for the treatment or prevention of a pulmonary disorder caused by the destruction of pulmonary alveoli comprising an effective amount of clarithromycin or a salt thereof and a pharmaceutically acceptable carrier.

Further, this invention provides a therapeutic or prophylactic agent for a pulmonary disorder caused by the destruction of pulmonary alveoli comprising as an effective ingredient, clarithromycin or a salt thereof.

In addition, this invention provides the use of clarithromycin or a salt thereof in the manufacture of a medicament for the treatment or prevention of a pulmonary disorder caused by the destruction of pulmonary alveoli.

In the method of treatment/prevention and the therapeutic/prophylactic pharmaceutical composition mentioned above, the efficacy of clarithromycin or a salt thereof is excellent where the pulmonary disorder is pulmonary emphysema or a pulmonary emphysema condition.

In the method of treatment/prevention and the therapeutic/prophylactic pharmaceutical composition mentioned above, the efficacy of clarithromycin or a salt thereof is especially excellent where the pulmonary emphysema condition is chronic obstructive pulmonary disease.

This invention also provides an in vivo method for reducing the cell counts of macrophages and/or neutrophiles in an mammal, the method comprising administering to the mammal, clarithromycin or a salt thereof in an amount sufficient to reduce the cell counts.

EFFECTS OF THE INVENTION

According to this invention, it has been demonstrated that clarithromycin or a salt thereof is effective as a therapeutic or prophylactic agent for a pulmonary disorder caused by the destruction of pulmonary alveoli.

BEST MODE FOR CARRYING OUT THE INVENTION

As used in the present specification, the term "pulmonary disorder caused by the destruction of pulmonary alveoli" refers to a pulmonary disease triggered by the destruction of the cells of pulmonary alveoli due to smoking, air pollution, noxious gas, aging or the like. Especially, of note is "pulmonary emphysema (condition)" by which owing to the destruction of pulmonary alveoli, the pulmonary alveor wall disintegrates to cause the adhesion of adjoining pulmonary alveoli and to form a cavity. In the pulmonary emphysema condition, the pulmonary alveoli of the peripheral respiratory tract are further destroyed, resulting in the obstructive disorder of airflow. This symptom is classified into "chronic obstructive pulmonary disease." The diseases displaying symptoms that are characterized by the aforementioned pulmonary alveoli destruction are collectively referred to as "pulmonary disorder caused by the destruction of pulmonary alveoli." These pulmonary disorders may often be accompanied by infections.

Clarithromycin used in this invention is a known compound; and its detailed description (production method, antibacterial activity, etc.) is disclosed in, for example, Japanese Published Patent Application Sho 61-52839 (JP61052839B). The whole of its disclosure is thus incorporated in the present Specification by reference. As used herein, the term "a salt of clarithromycin" refers to a pharmaceutically acceptable salt of clarithromycin. Specifically, there are mentioned the salts with organic acids such as tartaric acid, citric acid, stearic acid, and succinic acid; the salt with methanesulfonic acid; the salt with aminoethanesulfonic acid; and the salts with amino acids such as aspartic acid and glutamic acid. In place of clarithromycin a pharmaceutically acceptable derivative thereof may be used in this invention. This derivative refers to one that bears the basic skeleton of clarithromycin which has been derivatized and that displays the same pharmacological function as does clarithromycin. The particularly useful derivative is an ester of clarithromycin that experiences hydrolysis in vivo to release clarithromycin. These derivatives are also referred to as "prodrug(s)" and particular esters are well known to one skilled in the art.

When clarithromycin is used in this invention, it may be formulated into standard pharmaceutical preparations. Specifically, clarithromycin or a salt thereof is compounded with a pharmaceutically acceptable carrier (e.g., an excipient, binder, disintegrating agent, flavoring agent, emulsifier, diluent, and solubilizer) to prepare a pharmaceutical composition. This pharmaceutical composition may be administered to a mammal in the form of a preparation that is suitable for an oral or parenteral route, including tablets, pills, powders, granules, capsules, solutions, emulsions, suspensions, injectables, suppositories, inhalants and transdermals.

In producing these preparations, there may be added a solvent, a solubilizer, an isotonicating agent, a preservative, an antioxidant, an excipient, a binder, a lubricant, and a stabilizer.

Specifically, the solvents include water, physiological saline, etc.; the solubilizers include ethanol, polysorbates, cremophor, etc.; the excipients include lactose, starch, crystalline cellulose, mannitol, maltose, calcium hydrogenphosphate, light anhydrous silicic anhydride, calcium carbonate, etc.; the binders include starch, polyvinylpyrrolidone, hydroxypropyl cellulose, ethyl cellulose, carboxymethylcellulose, gum arabic, etc.; the disintegrating agents include starch, calcium carboxymethylcellulose, etc.; the lubricants include magnesium stearate, talc, hydrogenated oils, etc.; and the stabilizers include lactose, mannitol, maltose, polysorbates, macrogols, polyoxyethylene hydrogenated castor oil, etc.

To the preparations, there may be added glycerol, dimethylacetamide, 70% sodium lactate, a surfactant, and a basic substance (e.g., sodium hydroxide, ethylenediamine, ethanolamine, sodium carbonate, arginine, meglumine, and Tris-aminomethane) where necessary.

As used herein, the term "effective amount" means an amount or an amount of composition sufficient to exert a desired pharmacological effect when clarithromycin or a salt thereof, preferably as a pharmaceutical composition, is administered to a mammal in need of treatment or prevention. When clarithromycin or a salt thereof is to be used for the treatment purpose, the desired pharmacological effect means that the cure or alleviation of the symptom can be achieved in the mammal showing the developed symptom. When clarithromycin or a salt thereof is to be used for the prevention purpose, the desired pharmacological effect means the inhibition of the crisis in a mammal. In this case, preventive administration is conducted to the mammal suspected of potential crisis or having high risk of crisis prior to such crisis.

The dosage of clarithromycin or a salt thereof will be determined in consideration of the animal test results and other various circumstances so that the full dose may not exceed a certain level when it is administered singly or repeatedly. Needless to indicate, the actual dosage will vary depending on the method of administration and the conditions of the patient or the animal to be treated, specifically, within the range of from 10 to 1000 mg and on the age, the body weight, the gender, the susceptibility, the diet (feed), the administration time, any drug used together, or the degree of the symptom. The suitable dosage and the frequency of administration need to be determined by the medical specialist after optimum dose determination according to the aforementioned guideline.

EXAMPLES

This invention will be concretely described further by referring to a preparation example and test examples; however, the invention should not be limited to those examples.

Preparation Example 1

| | |
|---|---:|
| clarithromycin | 50 mg |
| lactose | 40 mg |
| corn starch | 49.75 mg |
| crystalline cellulose | 17 mg |
| carmellose calcium | 17 mg |
| hydroxypropyl cellulose | 5.25 mg |
| magnesium stearate | 1 mg |
| total | 180 mg |

Clarithromycin, lactose, corn starch, crystalline cellulose, and carmellose calcium were uniformly mixed. To this was added a 10% hydroxypropyl cellulose aqueous solution. After blending the mixture, the granules were dried and sieved with a 30M-screen to make uniform granules. Magnesium stearate was added to the granules and it was compressed to form tablets.

The pharmacological action of clarithromycin (improvement to a pulmonary emphysema condition) will be next explained by way of test examples.

Test Example 1

Pharmacological Effect in Model Mice with Tobacco Smoke-induced Pulmonary Emphysema The model mice with tobacco smoke-induced pulmonary emphysema mimicking human pulmonary emphysema were constructed according to the method as described in Hautamaki, R. D. et al., Science 1997, 277:2002-2004 or Shapiro, S. D. et al., Am. J. Pathol (2003) 163:2329-2335. Specifically, C57black/6 female mice of 12-weeks old were exposed to tobacco smoke at two cigarettes per day, 6 days per week for 6 months.

Administration of clarithromycin was carried out orally at the rate of 25, 50 or 100 mg/body weight twice daily (morning and evening) during the tobacco smoke exposure period. The plasma $AUC_{0-\infty}$ of clarithromycin obtained when 50 mg/kg was singly administered to the mice was 2.677 µg·hr/ml while the plasma $AUC_{0-\infty}$ of clarithromycin obtained when 200 mg of clarithromycin was singly administered to a normal human subject was 8.98 µg·hr/ml. The former concentration was substantially lower than the latter one and was an adequate concentration to be used clinically.

The index of the improvement to the pulmonary emphysema condition followed the method as described in Hautamaki, R. D. et al., ibid. or Shapiro, S. D. et al., ibid.

Hematoxylin eosin-stained pathological specimens were prepared from the model mice and ten visual fields under a microscope were randomly selected, where the average sizes of pulmonary alveoli were measured. An increase in the average size of pulmonary alveolus is considered as an index of the destruction of pulmonary alveoli, i.e., the pulmonary emphysema condition.

Table 1 shows the improvement factor of pulmonary emphysema in the model mice with tobacco smoke induced pulmonary emphysema. Six months' smoking (i.e., exposure to tobacco smoke) increased the pulmonary emphysema rate by 20% relative to the non-smoking group (control). The pulmonary emphysema was improved by 47% in the group administered with clarithromycin (25 mg/kg) and by a maximum of up to 87% in the group administered with clarithromycin (50 mg/kg). These results indicate that clarithromycin is effective against pulmonary emphysema (or pulmonary emphysema condition).

TABLE 1

| | pulmonary alveolus size (µm) | statistical significance | pulmonary emphysema rate (%) | improvement factor (%) |
|---|---|---|---|---|
| non-smoking | 32.21 ± 0.507 | | 0 | |
| smoking + solvent | 38.51 ± 0.765 | 0.0004 (vs. non-smoking) | 20 | 0 |
| smoking + CAM (25 mg/kg) | 35.60 ± 1.425 | 0.1001 (vs. smoking) | 10.6 | 47 |
| smoking + CAM (50 mg/kg) | 33.16 ± 0.890 | 0.0046 (vs. smoking) | 3 | 85 |
| smoking + CAM (100 mg/kg) | 34.35 ± 0.936 | 0.0092 (vs. smoking) | 6.7 | 66.5 |

(mean ± SE)

The cell counts of inflammatory cells (macrophages and neutrophiles) in the bronchoalveolar lavage fluids after six months' exposure were measured to provide an index of the inflammatory condition in the model mice with tobacco smoke-induced pulmonary emphysema. The results are shown in FIG. 1A and FIG. 1B.

The cell counts of macrophages and neutrophiles increased as the pulmonary emphysema progressed. These cells produce the proteases that are involved in pulmonary emphysema. These cell increases exacerbate the pulmonary emphysema. Administration of clarithromycin reduced the cell counts of macrophages and neutrophiles in a dose-dependant manner. This result indicates that clarithromycin inhibits inflammation reaction and suppresses the progression of pulmonary alveoli destruction.

It has been reported that as pulmonary emphysema progresses, pulmonary functions deteriorate. It has also been known that the pulmonary compliance, which is an index of pulmonary functions, increases in model mice with tobacco smoke-induced pulmonary emphysema. Thus, the pulmonary compliance was measured in the model mice with tobacco smoke-induced pulmonary emphysema after six months' exposure. The result is shown in FIG. 2.

As the pulmonary emphysema progressed, the pulmonary compliance (the index of pulmonary functions) was increasing in the model mice with tobacco smoke-induced pulmonary emphysema; however, the pulmonary compliance recovered upon the administration of clarithromycin. This result was in accord with the improvement of the pulmonary emphysema ratio as well as with the decrease in the number of the inflammatory cells, and it indicates that the clarithromycin administration is useful for the treatment of pulmonary emphysema (or pulmonary emphysema condition).

INDUSTRIAL APPLICABILITY

According to this invention, clarithromycin or a salt thereof is effective as a therapeutic or prophylactic agent for a pulmonary disorder caused by the destruction of pulmonary alveoli.

BRIEF DESCRIPTION OF THE DRAWINGS

FIG. 1A and FIG. 1B show the cell counts of inflammatory cells (macrophages and neutrophiles) in bronchoalveolar lavage fluids from model mice with tobacco smoke-induced pulmonary emphysema after six months' exposure. FIG. 1A shows the cell count of macrophages. FIG. 1B shows the cell count of neutrophiles.

FIG. 2 shows the results of pulmonary compliance measured in the model mice with tobacco smoke-induced pulmonary emphysema after six months' exposure.

The invention claimed is:

1. A method for suppressing the progression of the destruction of pulmonary alveoli in pulmonary emphysema in a mammal in need of such suppression, the method consisting of administering to the mammal, an effective amount of clarithromycin or a salt thereof for a period sufficient to suppress the progression in said mammal with pulmonary emphysema.

2. The method according to claim 1, wherein the clarithromycin or a salt thereof is administered as a composition with a pharmaceutically acceptable carrier.

3. The method according to claim 2, wherein the composition further comprises one or more of a solvent, a solublizer, an isotonicating agent, a preservative, an antioxidant, an excipient, a binder, a lubricant, and a stabilizer.

* * * * *